United States Patent [19]

Sumi et al.

[11] Patent Number: 5,534,255

[45] Date of Patent: Jul. 9, 1996

[54] MONOCLONAL ANTIBODY SPECIFIC TO HUMAN $\alpha_2$-PLASMIN INHIBITOR

[75] Inventors: Yoshihiko Sumi; Yukiya Koike, both of Hino; Yataro Ichikawa, Tokorozawa; Nobuhiko Yoshida, Tochigi-ken; Nobuo Aoki, Tokyo, all of Japan

[73] Assignee: Teijin Limited, Tokyo, Japan

[21] Appl. No.: 716,694

[22] Filed: Jun. 17, 1991

Related U.S. Application Data

[63] Continuation of Ser. No. 552,832, Jul. 16, 1990, abandoned, which is a continuation of Ser. No. 724,636, Apr. 16, 1985, abandoned.

[30] Foreign Application Priority Data

| Apr. 17, 1984 | [JP] | Japan | 59-75778 |
| May 1, 1984 | [JP] | Japan | 59-86101 |
| Oct. 12, 1984 | [JP] | Japan | 59-212587 |
| Oct. 18, 1984 | [JP] | Japan | 59-217312 |

[51] Int. Cl.$^6$ .......................... A61K 39/00; C07K 15/28
[52] U.S. Cl. ..................... 424/141.1; 424/152.1; 435/240.27; 435/172.2; 435/70.21; 530/388.1; 530/388.22; 530/388.25; 530/864; 530/866
[58] Field of Search .......................... 435/7.1, 7.4, 7.94, 435/13, 176, 177, 184, 180, 172.2, 240.27, 810; 530/381, 382, 387, 388.1, 388.22, 388.25, 864, 866; 424/85.8, 141.1, 152.1, 70.21; 436/501, 512, 518, 523, 525, 527, 528, 531, 533, 534, 536, 538, 540, 548, 808, 811, 823; 735/107

[56] References Cited

U.S. PATENT DOCUMENTS

| 4,198,335 | 4/1980 | Collen | 260/112 B |
| 4,474,892 | 10/1984 | Murad et al. | 436/548 |
| 4,514,505 | 4/1985 | Canfield et al. | 436/548 |

FOREIGN PATENT DOCUMENTS 0896543  5/1983  France.

OTHER PUBLICATIONS

Chemical Abstracts, vol. 100, No. 1, Jan. 2, 1984 p. 241, ref. No. 2752d.

Chemical Abstracts, vol. 88, No. 21, May 22, 1978 p. 400, ref. No. 150074h.

Moroi et al, The Journal of Biological Chemistry, vol. 251, No. 19, 1976, pp. 5956–5965.

Kohler et al, Nature vol. 256, Aug. 7, 1975, pp. 495–497.

Sevier et al, Clinical Chemistry, vol. 27. No. 11, 1981, pp. 1797–1806.

*Primary Examiner*—Christine M. Nucker
*Assistant Examiner*—Laurie Scheiner
*Attorney, Agent, or Firm*—Wenderoth, Lind & Ponack

[57] ABSTRACT

This invention provides a monoclonal antibody or its fragment specific to a human $\alpha_2$-plasmin inhibitor, said antibody having the function of specifically blocking that site of the human $\alpha_2$-plasmin inhibitor which inhibits the fibrinolytic activity of plasmin, and of suppressing said fibrinolytic activity inhibiting function of said $\alpha_2$-plasmin inhibitor, and also a hybridoma capable of producing the monoclonal antibody. Said monoclonal antibody or its fragment is useful for the immunological determination of a human $\alpha_2$-plasmin inhibitor, the separation or recovery of a human $\alpha_2$-plasmin inhibitor from a liquid containing the human $\alpha_2$-plasmin inhibitor, and the treatment of a thrombotic disease.

6 Claims, 4 Drawing Sheets

MONOCLONAL ANTIBODY SPECIFIC TO HUMAN $\alpha_2$-PLASMIN INHIBITOR

This application is a continuation of now abandoned application Ser. No. 07/552,832, filed Jul. 16, 1990, which is a continuation of Ser. No. 06/724,636 filed on Apr. 16, 1985, abandoned.

BRIEF SUMMARY OF INVENTION

This invention relates to a monoclonal antibody specific to a human $\alpha_2$-plasmin inhibitor, or an $\alpha_2$-antiplasmin, particularly a monoclonal antibody which specifically blocks the reactive site of a human $\alpha_2$-plasmin inhibitor, i.e. that site of $\alpha_2$-plasmin inhibitor which inhibits the fibrinolytic activity of plasmin, and consequently suppresses the action of the human $\alpha_2$-plasmin inhibitor to inhibit the fibrinolytic activity of plasmin and promotes fibrinolysis by plasmin; a hybridoma capable of producing the monoclonal antibody; a process for producing the hybridoma; the use of the monoclonal antibody in immunological assay of human $\alpha_2$-plasmin inhibitor; and to the use of the monoclonal antibody in the separation and recovery of human $\alpha_2$-plasmin inhibitor.

BACKGROUND OF INVENTION

It is known that the human $\alpha_2$-plasmin inhibitor (to be abbreviated hereinafter as "human $\alpha_2$-PI") is a single-chain glycoprotein having a carbohydrate content of 11.7% and a molecular weight of about 67,000 which was first isolated in pure form from human plasma by Aoki and Moroi and acts as a strong inhibitor capable of instantaneously inhibiting the esterase activity of plasmin, a fibrinolytic enzyme [see Moroi & Aoki: The Journal of Biological Chemistry, 251, 5956–5965 (1976)].

On the other hand, human $\alpha_2$-PI has three functions. Firstly, it has a site of inhibiting the fibrinolytic activity of plasmin (in the present specification, this site is referred to as the "reactive site") [see B. Wiman & D. Collen: The Journal of Biological Chemistry, 254, 9291–9297 (1979)]. Secondly, it has a site combining with plasmin at the carboxyl group terminal [B. Wiman & D. Collen: European Journal of Biochemistry, 84, 573–578 (1978)]. Thirdly, it has a site combining with fibrin at the amino group terminal [Y. Sakata et al.: Thrombosis Research, 16, 279–282 (1979)].

If it is possible to provide a monoclonal antibody which selectively blocks the reactive site of human $\alpha_2$-PI among these three active sites, it will be very interesting in medicine for the treatment of thrombotic diseases and the like because the use of such a monoclonal antibody can directly suppress the activity of human $\alpha_2$-PI to inhibit fibrinolysis of plasmin and promote fibrinolysis by plasmin.

It is known that in clinical medicine, the level of human $\alpha_2$-PI in the blood decreases in disorders of parenchymatous liver cells, and it has been reported that the level of human $\alpha_2$-PI in blood shows a marked decrease in decompensated liver cirrhosis and fulminant hepatitis [see N. Aoki & T. Yamanaka: Clinica Chimica Acta, 84, 99–105 (1978)].

Recently, the chemical, physical and biological properties of human $\alpha_2$-PI have been elucidated in detail, and it has been found that human $\alpha_2$-PI specifically controls and regulates the fibrinolytic mechanism of plasmin and performs an important action on this mechanism [see, for example, N. Aoki & P. C. Harpel: "Seminars in Thrombosis and Hemostasis, 10, 24–41 (1984)].

Accordingly, the provision of a monoclonal antibody capable of blocking the reactive site of human $\alpha_2$-PI specifically would enable the amount of human $\alpha_2$-PI in blood to be accurately and easily measured, and would be quite useful for the prevention and diagnosis of various diseases.

The only literature reference which discloses a monoclonal antibody to human $\alpha_2$-PI is Belgian Patent Specification No. 896,543 laid-open on Aug. 16, 1983. This patent specification states that 23 monoclonal antibodies to $\alpha_2$-PI which can be classified into 11 antibody groups having different epitope specificities were obtained, but fails to determine which epitopes of $\alpha_2$-PI these monoclonal antibodies will specifically recognize and combine with.

It is a primary object of this invention therefore to provide a highly specific monoclonal antibody or its fragment having the function of specifically blocking the reactive site of human $\alpha_2$-PI which inhibits the fibrinolytic activity of plasmin and thereby suppressing the action of human $\alpha_2$-PI to inhibit the fibrinolytic activity of plasmin.

Another object of this invention is to provide a hybridoma which secretes such a monoclonal antibody and a process for its production.

Still another object of this invention is to provide a method of immunologically assaying $\alpha_2$-PI in an assay sample by using the aforesaid monoclonal antibody, and a reagent which can be used in this method.

Yet another object of this invention is to provide a selective adsorbent for $\alpha_2$-PI using the aforesaid monoclonal antibody, and a method of separating or recovering $\alpha_2$-PI by using the adsorbent.

Further objects and advantages of this invention will become apparent from the following description.

DETAILED DESCRIPTION OF INVENTION

Figure 1:
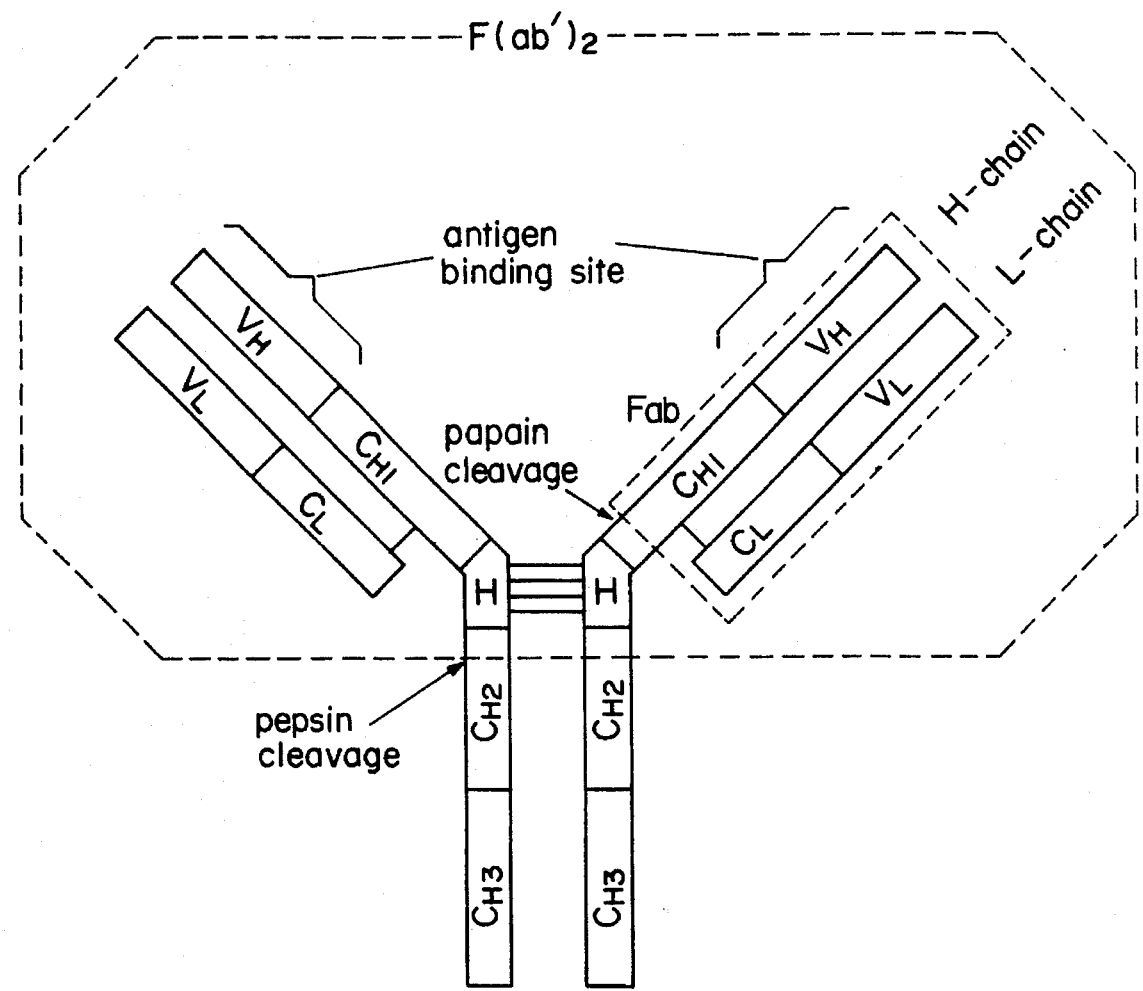
FIG. 1 is a partial structure of the monoclonal antibody of the invention.

According to one aspect of this invention, there is provided a monoclonal antibody specific to a human $\alpha_2$-PI, said antibody having the function of specifically blocking that site of the human $\alpha_2$-PI which inhibits the fibrinolytic activity of plasmin and suppressing the fibrinolytic activity inhibiting function of the human $\alpha_2$-PI.

According to this invention, the monoclonal antibody can be obtained by establishing a hybridoma cell line capable of producing said antibody, and cultivating the hybridoma.

The hybridoma capable of producing the monoclonal antibody of this invention can be produced by a technique known as the Köhler and Milstein method [Köhler and Milstein, Nature, 256,495–497 (1975)]. Specifically, a mammal such as a mouse is immunized with human $\alpha_2$-PI, and antibody-producing cells, for example, spleen cells, of this animal are fused with myeloma cells. The fused cells are screened by cloning for fused cells capable of producing the monoclonal antibody of this invention. For example, the fused cells produced are systematically screened for an antibody which reacts with human $\alpha_2$-PI fixed to microtiter plates. In this way, hybridoma cells which synthesize and secrete an antibody to $\alpha_2$-PI are selected The resulting hybridoma cells are cultivated in a medium containing or not containing serum. Antibodies to human $\alpha_2$-PI secreted in a supernatant from the culture fluid are examined on fibrin plates for the action of suppressing the fibrinolysis inhibiting activity of human $\alpha_2$-PI. As a result, a hybridoma capable of producing a monoclonal antibody having the action of specifically suppressing the fibrinolysis inhibiting activity of human $\alpha_2$-PI can be isolated.

The monoclonal antibody of this invention can be obtained from the product yielded by this hybridoma. The resulting monoclonal antibody acts monospecifically on the reactive site of human $\alpha_2$-PI.

The monoclonal antibody of this invention and the process for producing it will now be described in more detail.

(A) Isolation and purification of antigen

Human $\alpha_2$-PI used as an antigen is isolated in pure form from a human plasma sample by the aforesaid method of Aoki and Moroi.

(B) Immunization of mammals with human $\alpha_2$-PI

There is no particular restriction on the animals to be immunized, and various mammals such as mice, rats, guinea pigs, rabbits, sheep, goats, dogs and cats may be used. For the ease of handling, male Balb/c mice are generally used. Mice of other strains may also be used. The immunization should be planned, and the concentration of human $\alpha_2$-PI to be used in immunization should be selected, so that sufficient amounts of antigenically stimulated lymphocytes can be formed. For example, a mouse is intraperitoneally immunized several times with a small amount of human $\alpha_2$-PI at certain intervals, and the antigen is further administered intravenously several times to increase the titer of the antibody. Several days after the final immunization, antibody-producing cells, for example, lymphocytes, preferably spleen cells, are taken out from the immunized animals. The following description is given with regard to the use of spleen cells as the antibody-producing cells, but it should be understood that other antibody-producing cells isolated from immunized animals can equally be used for cell fusion.

(C) Cell fusion

The spleen is aseptically taken out from the immunized animal, and a spleen cell suspension is prepared from it. The spleen cells are then fused with myeloma cells taken from a suitable cell line in a fusion medium in the presence of a suitable fusion promoter. The myeloma cells used for fusion may be obtained from any mammals, but generally, those originated from the same kind of animal as the immunized animal are preferred. The preferred mixing ratio between the spleen cells and the myeloma cells is generally in the range of from about 20:1 to about 2:1, preferably from 10:1 to 2:1. Usually, the use of 0.5 to 1.5 ml of the fusion medium is suitable per about $10^8$ spleen cells. Suitable fusion media are, for example, physiological saline, buffered saline, a serum-free medium each of which contains the fusion promoter in a concentration of 30 to 70%.

Many myeloma cells suitable for cell fusion are known. In Examples to be given hereinafter, P3-X63-Ag8-U1 cells (to be abbreviated as P3-U1) [see D. E. Yelton et al.: Curent Topics in Microbiology and Immunology, 81, 1 (1978)]. They are an 8-azaguanine resistant cell line. They lack hypoxanthine-guanine phosphoribosyl transferase, and therefore do not survive in HAT medium (containing hypoxanthine, aminopterin and thymidine). Furthermore, since this cell line is of a non-secreting type which does not secrete an antibody itself, it is suitable for the production of the hybridoma contemplated by the present invention. Other myeloma cells may also be used. Examples include P3-NS1-1-Ag4-1, NS1-Ag4/1, P3-X63-Ag8, (MPCH-45, 6. TG1.7), SP2/0-Ag14, FO, X-63-Ag8-6.5.3, 210.RCY3.Ag1.2.3, S194/5XXO.BU.1, SKO-007, and GM15006TG-A12.

Polyethylene glycol having an average molecular weight of 1,000 to 4,000, for example, may be advantageously used as the fusion promoter. There can also be used other fusion promotors known in the art, such as Sendai virus. In the following Examples, polyethylene glycol having an average molecular weight of 1,540 was used.

(D) Detection of the fused cells

A mixture of the fused cells, non-fused spleen cells and non-fused myeloma cells is diluted in a separate receptacle (such as a microtiter plate) with a selective medium in which the non-fused myeloma cells cannot survive, and cultivated for a sufficient period of time to allow the non-fused cells to die (about 1 week). The culture medium may be one which is resistant to a drug such as 8-azaguanine and in which the non-fused myeloma cells cannot survive, for example the aforesaid HAT medium. In the selective medium, the non-fused myeloma cells die away. Since the non-fused spleen cells are non-tumoral, they die after a certain period of time (about 1 week). On the other hand, the fused cells can survive in the selective medium because they have both the tumor-bearing nature of the parent myeloma cells and the nature of the parent spleen cells.

(E) Determination of an antibody to human $\alpha_2$-PI in each receptacle

After the hybridoma cells are detected as stated above, the supernatant of the culture fluid is collected, and screened for an antibody to human $\alpha_2$-PI by enzyme linked immunosorbent assay (see, for example, A. H. W. M. Schuurs and B. K. van Weemen: Clin. Chim. Acta, 81, 1–40 (1977)].

(F) Selection of a hybridoma capable of producing an antibody having activity on human $\alpha_2$-PI The supernatant of the culture fluid obtained by cultivating the hybridoma producing an antibody to human $\alpha_2$-PI is concentrated and incubated with the human $\alpha_2$-PI for a fixed period of time. Plasmin is added to the mixture, and the mixture is placed on a fibrin plate. The area of the fibrin dissolved is measured. In this way, a hybridoma capable of producing an antibody having activity on human $\alpha_2$-PI is selected.

(G) Cloning of the hybridoma capable of producing the desired antibody

The hybridoma capable of producing the desired antibody can be cloned by a suitable method such as a limiting dilution method in two different ways. In one way, the hybridoma is cultivated in a suitable medium for a given period of time, and the monoclonal antibody produced by the hybridoma can be obtained from the supernatant of the culture fluid. In the other, the hybridoma can be intraperitoneally injected into a syngenic mouse. After a certain period of time, the monoclonal antibody produced by the hybridoma can be obtained from the blood and ascites of the host animal.

The resulting monoclonal antibody is highly specific to human $\alpha_2$-PI and has the function of specifically blocking the reactive site of human $\alpha_2$-PI, i.e. that site of human $\alpha_2$-PI which inhibits the fibrinolytic activity of plasmin, and suppressing the inherent action of human $\alpha_2$-PI to inhibit the fibrinolytic activity of plasmin.

In the present specification and the appended claims, the expression "blocks the reactive site" means the addition or combination of the monoclonal antibody to or with the the reactive site of human $\alpha_2$-PI in such a way that the monoclonal antibody recognizes the reactive site itself or any of the epitopes of human $\alpha_2$-PI thereby to cause the reactive site to lose activity.

It is believed that the monoclonal antibody provided by this invention, as other antibodies do, has in its variable region an antigen binding site capable of performing the aforesaid function.

The resulting monoclonal antibody is cleaved by the Porter's method [see R. R. Porter, Biochemical Journal, 73, 119–126 (1959)] using papain, a proteolytic enzyme, and a partial structure surrounded by a dotted line in FIG. 1 of the accompanying drawings and marked "Fab" is isolated.

The partial structure Fab of the monoclonal antibody is examined on a fibrin plate for its action of suppressing the activity of the human $\alpha_2$-PI to inhibit the fibrinolytic activity of plasmin. This leads to the determination that even the partial structure Fab alone of the monoclonal antibody has the function of specifically suppressing the activity of human $\alpha_2$-PI to inhibit the fibrinolytic activity of plasmin.

According to another aspect, therefore, there is provided a monoclonal antibody fragment which comprises at least the Fab region of a monoclonal antibody being specific to a human $\alpha_2$-plasmin inhibitor and having the function of specifically blocking that site of the human $\alpha_2$-plasmin inhibitor which inhibits the fibrinolytic activity of plasmin, i.e. the reactive site, and which has the function of suppressing the action of the human $\alpha_2$-plasmin inhibitor to inhibit the fibrinolytic activity of plasmin. Such a fragment includes, for example, not only a papain-cleaved fragment but also other fragments containing the Fab region obtained after cleavage with trypsin, plasmin, etc. The trypsin and plasmin cleavage sites are shown by arrows in FIG. 1.

The monoclonal antibody of the invention or its Fab-containing fragment produced as above can be used to determine $\alpha_2$-PI in a biological sample such as a human plasma sample because it has the function of specifically blocking the reactive site of human $\alpha_2$-PI. One previously known method of assaying $\alpha_2$-PI is an immunodiffusion method involving the use of an antiserum to human $\alpha_2$-PI [N. Aoki and I. Yamanaka: Clinica Chimica Acta, 84, 99–105 (1978)]. Another method is to add an excess of plasmin to an assay sample and measure the activity of remaining plasmin not bound to $\alpha_2$-PI [A. C. Tiger-Nilsson et al.: Scand. J. Clin. Lab. Invest., 37, 403–409 (1977)].

In practicing the former, it is extremely difficult to obtain an antiserum having a constant activity because the antiserum is of an animal origin. Hence, one must take the trouble of correcting the activity of the antiserum by using a standard substance. It also has the defect that long periods of time are required for immunodiffusion. According to the latter, the amount of human $\alpha_2$-PI is indirectly measured by measuring the amount of the remaining plasmin. Hence, it is susceptible to effects of various plasmin activity inhibiting substances present in the assay sample, and cannot possibly avoid errors in the amount of human $\alpha_2$-plasmin indirectly measured. Care must also be taken in this method about the purity or stability of the plasmin used.

In contrast, it has been found in accordance with this invention that the amount of human $\alpha_2$-PI in solution can be immunologically determined directly and accurately by the so-called "sandwich method" utilizing the monoclonal antibody or its Fab-containing fragment provided by this invention.

In still another aspect, therefore, the present invention provides a method of immunologically determining a human $\alpha_2$-plasmin inhibitor in an assay sample by using a primary antibody fixed to an insoluble solid carrier and a labelled secondary antibody (the so-called "sandwich method"), wherein the primary and secondary antibodies are anti-human $\alpha_2$-plasmin inhibitor antibodies or their Fab region-containing fragments which specifically recognize and combine with different epitopes of the human $\alpha_2$-plasmin inhibitor, and one of them is the monoclonal antibody or its Fab region-containing fragment of this invention.

Generally, a method of determining the presence or absence of an antigen or measuring its amount by using antibodies which combine with two different sites of the antigen is called the "sandwich method", and is described, for example, in Wide's Radioimmunoassay Methods, 199–206 (1970).

The immunological assay method of this invention is characterized by using anti-human $\alpha_2$-PI antibodies which specifically recognize and combine with different epitopes of human $\alpha_2$-PI as the two antibodies (primary and secondary antibodies), and particularly by using the monoclonal antibody of this invention which specifically blocks the reactive site of human $\alpha_2$-PI as one of these antibodies In the method of this invention, a fragment of the monoclonal antibody of the invention at least containing a Fab region having an antigen binding site (variable region) may also be used. Accordingly, it should be understood that unless otherwise stated, the term "antibody" used in the present specification also-denotes its fragment at least containing the Fab region.

Thus, the method of this invention enables human $\alpha_2$-PI in solution, for example in a plasma sample, to be always determined highly accurately with no difference in the quality of the reagent used. Since the amount of human $\alpha_2$-PI is directly measured, the method is not at all affected by foreign materials and can determine human $\alpha_2$-PI accurately within short periods of time. Accordingly, the present invention provides a new method of determining human $\alpha_2$-PI accurately and rapidly.

In the method of this invention, one (primary antibody) of the two antibodies is fixed to an insoluble solid carrier, and the other (secondary antibody) is used in the labelled state. The monoclonal antibody of this invention may be used as the primary antibody fixed to the insoluble solid carrier, or as the labelled secondary antibody. In either case, there is substantially no effect on the results of determination of human $\alpha_2$-PI.

The anti-human $\alpha_2$-PI antibody to be used in combination with the monoclonal antibody of this invention may be monoclonal or polyclonal if it can recognize and combine with a site of the human $\alpha_2$-PI other than the reactive site. Generally, it is convenient to utilize a monoclonal antibody which specifically recognizes and combines with a site of human $\alpha_2$-PI other than the reactive site and is secreted by a hybridoma obtained as a byproduct during the production of the monoclonal antibody of this invention.

The primary antibody may be fixed to the insoluble solid carrier by methods known per se. For example, a solution of the primary antibody and the insoluble solid carrier are contacted and left to stand, whereby the antibody is physically adsorbed on the carrier. It is also possible to combine the functional groups of the antibody, such as a carboxyl, amino or hydroxyl group, chemically with the insoluble solid carrier. Preferably, the surface of the carrier to which the primary antibody has been fixed is coated with a suitable substance such as bovine serum albumin in order to avoid non-specific combination with the secondary antibody or the assay sample.

Examples of the insoluble solid carrier used to fix the primary antibody include polymeric materials such as polystyrene, polyethylene, polypropylene, polyesters, polyacrylonitrile, fluorine-containing resins, nitrocellulose, crosslinked dextran, polysaccharides and agarose, inorganic materials such as glass and metal, and combinations of these. The solid carrier may be in various shapes, for example in the shape of a tray, sphere, fiber, particle, bead, disc, rod, receptacle, cell or test tube. Specific examples of the insoluble solid carrier are plastic receptacles, plastic beads, glass beads and metal particles.

The secondary antibody is labelled with radioisotopes, enzymes or luminescent substances. Examples of the radioisotopes are $^{125}I$, $^{131}I$, and $^{14}C$ and $^{3}H$. Examples of the enzymes are alkaline phosphatase, peroxidase, and beta-D-galactosidase. Examples of the luminescent substances are fluorescein isothiocyanate and tetramethyl rhodamine isothiocyanate. These are merely illustrative, and other labelling substances used in immunological assay may also be used. Combination of the labelling substances with the secondary antibody may be effected by methods known per se, for example by the methods described in G. S. David: Biochem. Biophys. Res. Commun., 48, 464–471 (1972), M. Imagawa et al., Anal. Lett., 16, 1509–1523 (1983) and M. Nishioka et al., Cancer Res., 32, 162–166 (1972).

The fixed primary antibody and the labelled secondary antibody are then brought into contact with an assay sample for determination of human $\alpha_2$-PI by a two-step method comprising contacting the sample first with the fixed primary antibody and then with the labelled secondary antibody, or by a one-step method comprising contacting the sample and the secondary antibody simultaneously with the primary antibody. The one-step method, however, is advantageous over the two-step method because it permits a simpler and more rapid determination of human $\alpha_2$-PI.

In the two-step method, the fixed primary antibody and the sample are contacted and reacted at a given temperature for a given period of time. During this time, the fixed primary antibody combines with the human $\alpha_2$-PI in the sample. After washing with a suitable washing liquor, the reaction product is contacted and reacted with a solution (e.g., an aqueous solution) of the labelled secondary antibody at a given temperature for a given period of time. The reaction product is washed with a suitable washing liquor, and the amount of the labelling substance present on the insoluble solid carrier is measured. The amount of the human $\alpha_2$-PI in the sample can be determined by comparing the amount of the labelling substance with a calibration curve drawn by using an assay sample containing human $\alpha_2$-PI in a known concentration.

In the one-step method, the fixed primary antibody is contacted and reacted with the assay sample and the labelled secondary antibody simultaneously, preferably with a mixture of the sample and the labelled secondary antibody at a given temperature for a given period of time. The product is then washed with a suitable washing liquor, and the amount of the labelling substance which is present on the insoluble solid carrier is measured as described above. As a result, the amount of human $\alpha_2$-PI in the sample can be determined.

According to the methods described above, the amount of human $\alpha_2$-PI in the assay sample can be measured easily with good reproducibility and a high accuracy. Human plasma, human serum and a supernatant from a cell culture are examples of the sample which can be assayed by the above methods.

For the practice of the above method, the present invention provides a reagent system comprising the primary antibody fixed to the insoluble solid carrier and the labelled secondary antibody. A kit may be formed from this reagent system and various auxiliary agents in order to use the reagent system efficiently and easily. Examples of the auxiliary agents include dissolving agents for dissolving the solid secondary antibody, washing agents for washing the insoluble carrier, substrates for measuring the enzyme activity of enzymes which may be used as labelling substances for the secondary antibody, and reaction stoppers therefor, which are normally used in reagent kits for immunological assay.

The use of the monoclonal antibody or its Fab-containing fragment of this invention enables human $\alpha_2$-PI in the assay sample to be determined accurately and easily and with good reproducibility by applying the "latex agglutination method".

The "latex agglutination method" is a method whereby an antibody is chemically and physically bonded to an immunologically inert synthetic resin, and agglutinating the synthetic resin through a soluble antigen.

In the present invention, this is carried out by bringing a primary antibody and a secondary antibody fixed simultaneously to fine particles of the same insoluble carrier or separately to fine particles of different insoluble carriers into contact with an assay sample in a liquid medium, and detecting changes which may occur by agglutination of the particles.

As the primary and secondry antibodies to be fixed to the insoluble fine carrier particles, anti-human $\alpha_2$-PI antibodies which specifically recognize and combine with different epitopes of human $\alpha_2$-PI are used as in the case of the "sandwich method" described hereinabove, and one of these antibodies is the monoclonal antibody of this invention which specifically blocks the reactive site of human $\alpha_2$-PI.

The insoluble carrier to which the primary and secondary antibodies are fixed may suitably be an immunologically inert insoluble substance, preferably polymers, silica, alumina or metals. Especially suitable insoluble carriers have approximately the same specific gravity as the liquid medium used in the method. Suitable fine particles have a particle diameter of generally 0.05 to 10 micrometers, preferably 0.2 to 2 micrometers, and the particle diameters are preferably as uniform as possible.

Fixation of the primary and secondary antibodies to insoluble carrier particles may be effected by physical adsorption or chemical bonding as in the case of the sandwich method described hereinabove. The primary and secondary antibodies may be simultaneously fixed to fine particles of the same carrier so that the two antibodies exist in the same carrier; or they may be fixed to fine particles of different carriers.

In determining human $\alpha_2$-PI in an assay sample using the fixed primary and secondary antibodies, these fixed primary and secondary antibodies are brought into contact with the sample in a liquid medium at a given temperature. As a result, the primary and secondary antibodies react with $\alpha_2$-PI, and the carrier particles to which these antibodies are fixed agglutinate together by the intermediary of $\alpha_2$-PI and grow. By detecting changes which occur by the agglutination of these particles and comparing them with a calibration curve prepared by using a sample of a known concentration, the amount of human $\alpha_2$-PI in the sample can be determined.

The changes by the agglutination of the particles can be detected as changes in the transmittance of light through the liquid medium, or changes in self-fluorescence generated by application of ultraviolet light. For example, the amount of human $\alpha_2$-PI in the assay sample can be determined by measuring the light transmittance of the liquid medium after a lapse of a certain period of time or the time which has elapsed until a predetermined transmittance is reached, and comparing the measured value with a calibration curve (standard cuve) prepared in advance.

Any liquid which is miscible with the assay sample may be used as the liquid medium in the above method. Generally, physiological saline, phosphate buffered saline, and Tris-buffered saline are suitable examples of the liquid medium. As required, glycine, albumin, sodium azide, etc. may be added to the liquid medium. The concentration of the fine carrier particles having the primary and secondary antibodies fixed thereto in the liquid medium is generally 0.002 to 10%, preferably 0.02 to 2%. The ratio of the fixed primary antibody to the fixed secondary antibody is generally from 0.01 to 100, preferably from 0.1 to 10.

According to this invention, a reagent system for use in the above measuring method is provided. Basically, this reagent system comprises a primary and a secondary antibodies fixed simultaneously to fine particles of the same insoluble carrier or separately to fine particles of different insoluble carriers, and as required may be combined with a washing agent, a reaction stopper, a diluting liquid, a standard substance, etc. to form a reagent kit.

The insoluble fine carrier particles having the primary antibody and/or the secondary antibody fixed thereto may be lyophilized to a powder; or they may be incorporated in the form of a suspension in the aforesaid liquid medium into the reagent system.

The monoclonal antibody or its FAb region-containing fragment in accordance with this invention can also be applied to the separation or recovery of human $\alpha_2$-PI from a liquid containing the human $\alpha_2$-PI because it has the function of specifically blocking the reactive site of human $\alpha_2$-PI.

Thus, according to still another aspect of this invention, there are provided a selective adsorbent for human $\alpha_2$-PI comprising an insoluble solid carrier and the monoclonal antibody or its Fab region-containing fragment of the invention fixed thereto, and a method for separating or recovering human $\alpha_2$-PI from a liquid containing human $\alpha_2$-PI, which comprises bringing said liquid containing human $\alpha_2$-PI into contact with the aforesaid selective adsorbent to adsorb human $\alpha_2$-PI on the adsorbent, and separating the adsorbent from said liquid, and as required, desorbing human $\alpha_2$-PI from the adsorbent and recovering it.

Generally, chromatography based on the utilization of the biological affinity of an adsorbent to the separation and purification of a biological substance is called affinity chromatography [Ichiro Chihata, Testsuya Tosa and Yushi Matsuo, "Experimental and Applied Affinity Chromatography" (Japanese-language publication), Kodansha Co., Ltd.].

The terms "affinity", "ligand", "insoluble solid carrier", and "adsorbent", as used herein, should be understood to have the following meanings.

Affinity: specific affinity between two substances.

Ligand: a substance having affinity for a substance to be adsorbed or purified.

Insoluble solid carrier: a solid support insoluble in water (excluding the ligand)

Adsorbent: the insoluble solid carrier to which the ligand is fixed.

Now, the selective adsorbent for human $\alpha_2$-PI and the method for separating or recovering human $\alpha_2$-PI from a liquid containing the human $\alpha_2$-PI, which are provided by this invention, will be described in detail.

The monoclonal antibody to human $\alpha_2$-PI or its Fab region-containing fragment in accordance with this invention is chemically bonded as a ligand to a suitable insoluble carrier (e.g., Sepharose), and the carrier is then packed into a column. The column is then equilibrated with a suitable buffer (for example, 50 mM Tris buffer, pH 7.4, 0.15M NaCl). A liquid containing human $\alpha_2$-PI to be treated (such as a human plasma or serum sample) is added to the resulting adsorbent to adsorb human $\alpha_2$-PI on the adsorbent. Impurities are then removed from the adsorbent by a suitable washing solution (for example, 50 mM Tris buffer, pH 7.4, 0.15M NaCl). Then, the amount of human $\alpha_2$-PI in a fraction which has passed through the column ("pass-through fraction") and a fraction which has been washed out from the column ("washed fraction") is measured. From the measured values, the degree of separation of human $\alpha_2$-PI from the sample liquid can be calculated.

Various substances can be used as the insoluble solid carrier used in the selective adsorbent of this invention. Preferably, it is made of, for example, agarose, polyacrylamide, cellulose, dextran, maleic acid polymer, or a mixture of any of these. The insoluble solid carrier may be in various forms, for example, in the form of a powder, granule, pellets, beads, film or fiber.

Fixation of the monoclonal antibody or its fragment to the insoluble solid carrier is generally carried out by chemically bonding it to the carrier. For example, it may be effected by activating Sepharose by the action of CNBr and fixing the antibody to it [R. Axén et al.: Nature, 214, 1302–1304 (1967)].

When the adsorbent having human $\alpha_2$-PI adsorbed thereon by contact with the liquid containing human $\alpha_2$-PI is separated from the liquid, the human $\alpha_2$-PI present in the liquid can be removed. If human plasma or serum is used as the liquid, human plasma or serum substantially free from human $\alpha_2$-PI can be obtained. Such human $\alpha_2$-PI-free human plasma or serum can be advantageously used, for example, in plasma or serum exchange therapy.

The adsorbent having human $\alpha_2$-PI adsorbed thereon and separated from the assay liquid may be subjected to a desorption treatment to elute human $\alpha_2$-PI from the adsorbent and recover it. The recovered human $\alpha_2$-PI can be used, for example, as a supplement in congenital $\alpha_2$-PI deficiency disease and liver diseases, or as a hemostat. The desorption treatment may be carried out by treating the adsorbent having human $\alpha_2$-PI adsorbed thereon with an eluent. An aqueous solution of ethylene glycol having a pH of 2.5 to 12.5, preferably 5.0 to 11.5, can be advantageously used as the eluent. Other examples of the eluent that can be used in the invention include an aqueous solution of glycerol, an aqueous solution of glycine, an aqueous solution of propionic acid, an aqueous solution of a thiocyanate salt, and an aqueous solution of guanidine.

The concentration of ethylene glycol in the aqueous ethylene glycol solution is advantageously 20 to 80%, preferably 40 to 60%. For pH adjustment, the aqueous solution may include suitable pH-adjusting agents, for example hydroxides such as sodium hydroxide or potassium hydroxide, salts such as Tris salts, phosphate salts or Veronal salt, acids such as hydrochloric acid, nitric acid, acetic acid, citric acid and oxalic acid, amines such as ethanolamine, ammonia, or urea. The desorption treatment is carried out at a temperature above the freezing point but not exceeding 37°

C. preferably at 2° to 10° C. The desorption treatment is performed by a column method, a batch method, etc. The time required for elution is desirably short, but may be up to about 2 days.

From the eluate containing the eluted human $\alpha_2$-PI, the human $\alpha_2$-PI can be separated and purified by methods known per se, for example by dialysis, concentration, or liquid chromatography.

As stated hereinabove, the monoclonal antibody or its Fab region-containing fragment provided by this invention has the function of specifically blocking the reactive site of human $\alpha_2$-PI, i.e. that site of human $\alpha_2$-PI which inhibits the fibrinolytic activity of plasmin, and suppressing the action of human $\alpha_2$-PI to inhibit the fibrinolytic activity of plasmin. Accordingly, if the monoclonal antibody or its fragment is administered to a patient in whom the fibrinolytic activity of plasmin is inhibited by the action of human $\alpha_2$-PI and thrombus is formed in the vessel, the inhibiting action of the human $\alpha_2$-PI is blocked and plasmin can directly act on the thrombus and dissolve it. The effect of the monoclonal antibody or its fragment of this invention to promote fibrinolysis of thrombus can be ascertained, for example, by the following two in vitro test. A first of these test is a lysis test in a purified system using a fibrin plate, and a second one is a lysis test on thrombus prepared by using plasma or blood. In the first test, the area of the fibrin plate dissolved by plasmin in the presence of human $\alpha_2$-PI and in the presence of human $\alpha_2$-PI and the monoclonal antibody or its fragment of this invention is measured, and compared with the area of the fibrin plate dissolved only in the presence of plasmin. In the second test, human plasma or blood is coagulated with thrombin, and the coagulated clot is suspended in human plasma or blood to which the monoclonal antibody or its fragment of this invention has been added. The time which elapses until the coagulated clot is dissolved is compared with that in the case of using normal human plasma or blood. It has been confirmed that as described in detail in Examples, in either of these tests, the fibrin plate or the coagulated clot is rapidly dissolved in the presence of the monoclonal antibody or its fragment of this invention.

The monoclonal antibody or its Fab region-containing fragment of this invention can therefore be used for the treatment of human thrombotic diseases including myocardial infarction, cerebral infarction, vein obstructive diseases and artery obstructive diseases.

The monoclonal antibody or its fragment of the invention may be administered parenterally, preferably intravenously. The dose varies depending upon the sex, age, condition, body weight, etc. of a patient to be treated. Generally, the dose may be about 0.01 to about 10 mg/kg of body weight daily as an amount effective for dissolving thrombus either once or several times a day. By the judgement of a physician, it may, of course, be administered in higher doses.

The monoclonal antibody or its fragment may be formulated into a form suitable for administration, for example an injectable solution, a drip, a lyophilized powder, together with a pharmaceutically acceptable carrier or diluent. Examples of the pharmaceutically acceptable carrier or diluent are water, buffers, blood isotonizing agents, stabilizers (e.g., human plasma albumin, mannitol), and human antibodies or their fragments. An injectable solution or a drip may be prepared by dissolving the monoclonal antibody or its fragment of this invention in physiological saline in a concentration of 0.001 microgram/ml to 100 ng/ml, and as required, further adding 0.01M sodium phosphate as a buffer, and 1% of mannitol and 0.1% of human serum albumin as stabilizers. The concentrations of the additional agents may be varied properly. As required, a human antibody or its fragment may be added. The injectable solution or drip may be prepared in the form of a solution or a lyophilized form. The lyophilized product may be dissolved in such a medium as pure water before use. The injectable solution, the drip, a lyophilized product thereof, and a solution of the lyophilized product should be prepared and stored aseptically.

The following Examples illustrate the present invention more specifically.

EXAMPLE 1

(1) Preparation of human $\alpha_2$-PI

In accordance with the method of Aoki and Moroi cited hereinabove, 7.7 mg of human $\alpha_2$-PI was obtained from 2,360 ml of human plasma (2) Immunization of mice Male Balb/c mice were immunized intraperitoneally with an emulsion of 100 micrograms of human $\alpha_2$-plasmin inhibitor and complete Freund's adjuvant twice at an interval of 21 days. Seven days and 88 days later, 30 micrograms of human $\alpha_2$-PI in physiological saline was additionally administered intravenously. Four days after the final immunization, the spleen cells were isolated for cell fusion.

(3) Preparation of a suspension of the spleen cells

The spleen cells were taken out aseptically and passed through a stainless steel mesh to obtain a suspension of the spleen cells. The cells were transferred to RPMI-1640 medium (a product of GIBCO) supplemented with 0.39 g/liter of L-glutamine, 0.2 g/liter of kanamycin sulfate and 2.0 g/liter of $NaHCO_3$. The cells which proliferated were washed three times with RPMI-1640 and again suspended in RPMI-1640 medium.

(4) Preparation of myeloma cells

Mouse myeloma cells, P3-U1, were cultivated in RPMI-1640 medium supplemented with 0.39 g/liter of L-glutamine, 0.2 g/liter of kanamycin sulfate, 2.0 g/liter of $NaHCO_3$ and 10% fetal calf serum (to be abbreviated as 10% FCS-RPMI-1640). At the time of cell fusion, the myeloma cells were in the log phase of cell fission.

(5) Cell fusion

The spleen cells and the myeloma cells were suspended in a ratio of 10:1 in serum-free RPMI-1640 medium, and then centrifuged at about 200 G for 5 minutes. The supernatant was removed, and the sediment was incubated together with 1 ml of [a 50% solution of polyethylene glycol having an average molecular weight of 1,540 (pH 8.2)] at 37° C. for 2 minutes. Then, 9 ml of serum-free RPMI-1640 medium was added, and the cells were again suspended carefully for 5 minutes. The suspension was centrifuged at about 200G for 5 minutes, and again suspended in 10% FCS-RPMI-1640 medium so that a concentration of $8\times10^6$ cells/ml was obtained. The suspension was then distributed on a 96-microwell plate (about 100 microliters per well). The fused cells were cultivated at 37° C. using 5% $CO_2$.

(6) Selection and cultivation of fused cells capable of producing an antibody to human $\alpha_2$-PI One day after cell fusion, HAT medium was added in an amount of 100 microliters per well. Thereafter, at intervals of 2 days, one half of the medium was exchanged with a fresh supply of HAT medium, and the cultivation was continued. Eight days later, the supernatant of the culture fluid of hybridoma cells was screened for antibodies to human $\alpha_2$-PI by the enzyme linked immunosorbent assay. The antigen used in the screening was human $\alpha_2$-PI, and the second antibody was alkali phosphatase-conjugated rabbit anti-mouse antibodies.

349 wells in total were found to be positive by the enzyme-linked immunosorbent assay, and thus to produce antibodies to $\alpha_2$-PI.

When it was observed that the proliferation of the cells was active, HT medium was added. The medium was exchanged with HT medium four times at intervals of one day. Thereafter, the cultivation was carried out by using ordinary 10% FCS-RPMI-1640 medium.

EXAMPLE 2

Selection of fused cells producing antibodies to human $\alpha_2$-PI:

The fused cells producing antibodies to human $\alpha_2$-PI was screened by the following procedure for fused cells which had the action of suppressing the fibrinolysis inhibiting activity of human $\alpha_2$-PI.

The fused cells in each well were cultivated in 10% FCS-RPMI-1640 medium until the number of the cells reached about $2 \times 10^7$. The cells were then centrifuged at about 200 G for 5 minutes. The supernatant was removed, and the cells were washed with 10 ml of serum-free RPMI-1640 medium, and further centrifuged at about 200G for 5 minutes. The supernatant was removed, and the cells were suspended in 10 ml of a mixed serum-free medium (to be abbrevaited as "MITES medium") composed of RPMI-1640 medium supplemented with 5.0 ml/liter of 2-mercaptoethanol, 7.5 ml/liter of insulin, 5.0 ml/liter of transferrin, 5.0 ml/liter of ethanolamine, 5.0 ml/liter of sodium selenite, 0.39 g/liter of L-glutamine, 0.2 g/liliter of kanamycin sulfate, and 2.38 g/liter of Hepes, Dulbecco's MEM, and Ham's F-12 (2:1:1), and cultivated for 3 days.

The supernatant of the culture fluid was recovered, and concentrated to 25 times. To 25 microliters of the concentrate was added 0.4 microgram of human $\alpha_2$-PI, and the mixture was incubated at 37° C. for 30 minutes. Then, 0.025 unit of plasminogen and 0.031 unit of urokinase were added, and the amount of the entire solution was adjusted to 40 microliters. Ten microliters of it was placed on a fibrin plate. The fibrin plate was left to stand at a temperature of 37° C. and a humidity of more than 95% for 18 hours, and the area of fibrin dissolved was measured.

The results show that the fibrinolysis inhibiting activity of human $\alpha_2$-PI added to the antibodies produced by 1D10 fused cells was completely suppressed.

EXAMPLE 3

Cloning of fused cells:

The fused cells (1D10) which were found positive in the test for the activity of the antibodies to human $\alpha_2$-PI were cloned by the following procedure.

The 1D10 cells were diluted so that each well of a 96-well microtiter plate contained 0.9 cell. Thymus cells of Balb/c mice were added as feeder cells and distributed on the plate and cultivated in 10% FCS-RPMI-1640 medium. Microscopic observation showed exactly single cell colonies formed. The supernatant of the culture fluid of the fused cells was screened by the enzyme-linked immunosorbent assay for antibodies to human $\alpha_2$-PI.

Twenty-six wells in total were found to be positive by the enzyme-linked immunosorbent assay, and thus to produce monoclonal antibodies to human $\alpha_2$-PI.

Purification of monoclonal antibodies:

In order to produce large amounts of monoclonal antibodies to human $\alpha_2$-PI, about $10^7$ fused cells were intraperitoneally injected into Balb/c mice pre-treated with pristane. About one week later, the antibodies were isolated from the ascites fluid and purified by the method of Ey et al. [P. L. Ey, S. J. Prowse and C. R. Jenkin, Immunochemistry, 15, 429–436 (1978)]. Twenty milligrams of monoclonal antibodies to human $\alpha_2$-PI were obtained from 2.5 ml of the ascites fluid.

Characterization of the purified monoclonal antibodies:

The particular classes of the purified monoclonal antibodies were determined by the Ouchterlony gel diffusion test using class-specific antimouse-immunoglobulin antisera. The results given in Table 1 show that many of the antibodies to human $\alpha_2$-PI are of the H-chain $\gamma_1$ type and L-chain $\kappa$ type.

TABLE 1

| Antibody | IgG$_1$ | IgG$_2$a | IgM | K |
| --- | --- | --- | --- | --- |
| 1B10C4 | | + | | + |
| 1B10G11 | | + | | + |
| 1D10C1 | + | | | + |
| 1D10F10 | + | | | + |
| 1D10-1F5 | + | | | + |
| 1D10B11 | + | | | + |
| 1D10-2H8 | + | | | + |

The hydridomas, 1B10G11 and 1D10B11, have been deposited with the Fermentation Research Institute and have been assigned accession numbers 1782 (FERM BP-1782) and 1781 (FERM BP-1781), respectively.

EXAMPLE 4

Suppression of the activity of human $\alpha_2$-PI by antibodies to human $\alpha_2$-PI:

One microgram of human $\alpha_2$-PI and 5 microgram of each of the monoclonal antibodies indicated above were dissolved in 50 microliters of 0.05M phosphate-buffered physiological saline (to be abbreviated as PBS), and incubated at 37° C. for 30 minutes. Then, 0.025 unit of plasminogen and 0.031 unit of urokinase were added, and the amount of the solution was adjusted to 60 microliters. Ten microliters of it was placed on a fibrin plate. The fibrin plate was left to stand at a temperature of 37° C. and a humidity of more than 95% for 18 hours, and the area of fibrin dissolved was measured. The results are shown in Table 2.

The values shown in Table 2 are relative values obtained by taking the area dissolved with 0.025 unit of plasminogen and 0.031 unit of urokinase as 100%.

TABLE 2

| Antibody | Area dissolved (%) |
| --- | --- |
| 1D10C1 | 100 |
| 1D10F10 | 97 |
| 1D10-1F5 | 109 |
| 1D10B11 | 85 |
| 1D10-2H8 | 100 |
| 1D10-1H2 | 70 |

EXAMPLE 5

Effect of the monoclonal antibody to human $\alpha_2$-PI upon combining of human $\alpha_2$-PI with fibrin:

0.01 μM of $I^{125}$-labelled human $\alpha_2$-PI and 0.05 μM of a monoclonal antibody to $\alpha_2$-PI were incubated at 37° C. for 30 minutes together with 2% bovine serum albumin—0.05M Tris buffer (pH 7.4)—0.15M NaCl, and then left to stand overnight at 4° C. To the antigen-antibody reaction mixture were added 2.5 mM $CaCl_2$, 7 μM of a fibrinogen fraction and 2 units/ml of thrombin, and the total amount of the mixture was adjusted to 100 microliters. It was incubated at 37° C. for 30 minutes. Formation of a coagulated material (fibrin clot) was observed. Thirty minutes later, 100 microliters of 200 mM EDTA was added, and the calcium ion was removed. Then, the coagulated material was taken out by winding it about a slender stick made of bamboo. The coagulated material was washed three times with a washing liquor [2% BSA, 0.05M Tris buffer (pH 7.4), 0.15M NaCl, 2 mM EDTA]. Finally the coagulated material was separatred from the bamboo stick and recovered in a test tube. The radioactivity (cpm) of the coagulated material was then measured. The radioactivity of the coagulated material relative to the radioactivity of the original reaction mixture in each case is shown in Table 3.

Table 3 also gives the result obtained by using an ordinary commercial mouse IgG used as a comparative antibody.

TABLE 3

| Antibody | Percent combination |
|---|---|
| 1B10C4 | 14.3 |
| 1B10G11 | 16.2 |
| 1D10C1 | 17.4 |
| 1D10F10 | 17.8 |
| 1D10-1F5 | 17.1 |
| 1D10B11 | 17.6 |
| 1D10-2H8 | 18.5 |
| Mouse IgG | 14.0 |

The results indicate that the monoclonal antibodies to human $\alpha_2$-PI tested are monoclonal antibodies which do not recognize the fibrin binding site of human $\alpha_2$-PI.

EXAMPLE 6

Selection of a monoclonal antibody which recognizes the reactive site of human $\alpha_2$-PI:

In this Example, the effect of a monoclonal antibody to human $\alpha_2$-PI upon the inactivation of plasmin by human $\alpha_2$-PI was examined.

0.6 microgram of $\alpha_2$-PI and 6.6 micrograms of a monoclonal antibody to $\alpha_2$-PI were dissolved in 60 microliters of 2% bovine serum albumin solution [0.05M Tris buffer (pH 7.4), 0.15M NaCl], and incubated at 37° C. for minutes, followed by standing overnight at 4° C.

The reaction mixture was mixed with 20 microliters of a plasmin solution (0.47 μM), and 0.05M Tris buffer (pH 7.4) and 0.15M NaCl were added, and the total amount of the liquid was adjusted to 500 microliters. For each monoclonal antibody, two samples of this mixture were prepared, and incubated at 37° C. for 2 minutes and 20 minutes, respectively. Then, 200 microliters of an aqueous solution of 3.5 mM synthetic substrate S-2251 (H-D-valyl-L-leucyl-L-lysyl-p-nitroanilide dihydrochloride) was added, and by a spectrophotometer (Beckman, DU-8), changes in absorbance at a wavelength of 405 nm per minute were measured. As controls, changes in absorbance were similarly examined with respect to a sample resulting from the reaction of plasmin alone, and a sample obtained by the reaction of human $\alpha_2$-PI with plasmin in the absence of monoclonal antibody. The results are shown in Table 4.

TABLE 4

| | Change in absorbance (405 nm/min.) | |
|---|---|---|
| Antibody | Reaction time 2 minutes | Reaction time 20 minutes |
| 1B10C4 | 0.008 | — |
| 1B10G11 | 0.012 | — |
| 1D10C1 | 0.140 | 0.108 |
| 1D10F10 | 0.145 | 0.110 |
| 1D10-1F5 | 0.150 | 0.100 |
| 1D10B11 | 0.162 | 0.109 |
| 1D10-2H8 | 0.150 | 0.103 |
| Plasmin alone | 0.122 | 0.102 |
| Human $\alpha_2$-PI + plasmin | 0.026 | 0.005. |

The results obtained in Examples 5 and 6 demonstrate that the monoclonal antibodies of this invention specifically recognize the reactive site of human $\alpha_2$-PI, and do not recognize the plasmin binding site and fibrin biding site of human $\alpha_2$-PI.

EXAMPLE 7

Cleavage by papain of a monoclonal antibody which recognizes the reactive site of human $\alpha_2$-PI:

One milligram of the monoclonal antibody 1D10C1 described in the preceding Example which specifically recognizes the reactive site of human $\alpha_2$-PI was dissolved in 300 microliters of a solution [2 mM EDTA, 12.5 mM cysteine, 50 mM Tris buffer (pH 7.4), 0.15M NaCl], and 100 microliters of a papain solution in a concentration of 1 mg/ml was added and reacted at 37° C. for 18 hours.

The reaction mixture was subjected to liquid chromatography, and the Fab component of the antibody was separated. By SDS-polyacrylamide gel electrophoresis, its molecular weight was measured under reducing and non-reducing conditions. It was ascertained that the Fab component was composed of a fragment having a molecular weight of about 23,000 from the amino group terminal of the heavy chain of the antibody and the entire light chain having a molecular weight of about 23,000.

EXAMPLE 8

Suppression of the activity of human $\alpha_2$-PI by the Fab component of the antibody to human $\alpha_2$-PI:

One microgram of human $\alpha_2$-PI and 3 micrograms of each of the monoclonal antibodies indicated in Table 5 were dissolved in 50 microliters of 0.05M PBS and incubated at 37° C. for 30 minutes. Then, 0.025 unit of plasminogen and 0.031 unit of urokinase were added, and the total amount of the solution was adjusted to 60 microliters. Ten microliters of it was placed on a fibrin plate, and the fibrin plate was left to stand at a temperature of 37° C. and a humidity of more than 95%. The area of fibrin dissolved was measured. The results are shown in Table 5. The values shown in the following table are relative values obtained by taking the area of fibrin dissolved with 0.025 unit of plasminogen and 0.031 unit of urokinase as 100%.

TABLE 5

| Antibody | Area dissolved (%) |
| --- | --- |
| 1D10C1 | 100 |
| 1D10C1 Fab | 100 |

Furthermore, by the same procedure as in Example 6, the suppression of the activity of human $\alpha_2$-PI by the Fab component of this monoclonal antibody was examined.

0.6 microgram (9 picomoles) of $\alpha_2$-PI and 40 picomoles of a monoclonal antibody to human $\alpha_2$-PI were dissolved in 60 microliters of a 2% bovine serum albumin solution [0.05M Tris buffer (pH 7.4), 0.15M NaCl], and incubated at 37° C. for 30 minutes, followed by standing overnight at 4° C.

The reaction mixture was mixed with 20 microliters of a plasmin solution (0.47 μM), and total amount of the solution was adjusted to 500 microliters. Then, microliters of an aqueous solution of 3.5 mM synthetic substrate S-2251 was added, and changes in absorbance at a wavelength of 405 nm per unit time were measured by a spectrophotometer (Hitachi 100-50). As controls, changes in absorbance were likewise examined with respect to a sample obtained by reacting plasmin alone, and a sample obtained by reacting both human $\alpha_2$-PI and plasmin. The results are shown in Table 6.

TABLE 6

| Antibody | Changes in absorbance (405 nm/min.) |
| --- | --- |
| 1D10C1 | $24.8 \times 10^{-5}$ |
| 1D10C1 Fab | $26.0 \times 10^{-3}$ |
| Plasmin alone | $24.0 \times 10^{-3}$ |
| human $\alpha_2$-PI plasmin | $8.4 \times 10^{-3}$ |

The results obtained in Example 8 show that the monoclonal antibody having the Fab region in accordance with this invention specifically recognizes the reactive site of human $\alpha_2$-PI and suppresses the fibrinolysis inhibiting function of human $\alpha_2$-PI.

EXAMPLE 9

Cleavage by pepsin of a monoclonal antibody which recognizes the reactive site of human $\alpha_2$-PI:

0.39 mg of the monoclonal antibody 1D10C1 described in the preceding Example which specifically recognizes the reactive site of human $\alpha_2$-PI was dissolved in 0.5 ml of 0.1M sodium acetate (pH 4.6), and 1.0 ml of a pepsin solution (0.1M sodium acetate, pH 4.6) having a concentration of 0.33 mg/ml was added and reacted at 37° C. for 14 hours.

The reaction mixture was subjected to liquid chromatography and the F(ab')2 component was separated. The molecular weight of this component was measured by SDS-polyacrylmide gel electrophoresis under reducing and non-reducing conditions. It was found to be a F(ab')2 component composed of a fragment having a molecular weight of about 28,000 from the amino group terminal of the heavy chain, and the entire light chain having a molecular weight of about 23,000.

EXAMPLE 10

Suppression of the activity of human $\alpha_2$-PI by the F(ab')2 component of an antibody to human $\alpha_2$-PI:

One microgram of human $\alpha_2$-PI and 2 micrograms of a monoclonal antibody were dissolved in 50 microliters of 0.05M PBS and incubated at 37° C. for 30 minutes. Then, 0.025 unit of plasminogen and 0.031 unit of urokinase were added, and the total amount of the solution was adjusted to 60 microliters. Ten microliters of it was placed on a fibrin plate, and the fibrin plate was left to stand at a temperature of 37° C. and a humidity of more than 95% for 18 hours. The area of fibrin dissolved was measured. The results are shown in Table 7. The values shown in the following table are relative values obtained by taking the area dissolved by 0.025 unit of plasminogen and 0.031 unit of urokinase as 100%.

TABLE 7

| Antibody | Area dissolved (%) |
| --- | --- |
| 1D10C1 | 100 |
| 1D10C1 F(ab')2 | 100 |

By the same procedure as in Example 6, the suppression of the activity of human $\alpha_2$-PI by the F(ab')2 component of this monoclonal antiibody was examined.

0.6 microgram (9 picomoles) of $\alpha_2$-PI and 40 picomoles of the monoclonal antibody to $\alpha_2$-PI were dissolved in 60 microliters of a 2% bovin serum albumin solution [0.05M Tris buffer (pH 7.4), 0.15M NaCl], and incubated at 37° C. for 30 minutes, followed by standing overnight at 4° C.

The reaction mixture was mixed with 20 microliters of a plasmin solution (0.47 μM), and 0.05M Tris buffer (pH 7.4) and 0.15M NaCl were added, and the total amount of the solution was adjusted to 500 microliters. Then, 200 microliters of an aqueous solution of 3.5 mM synthetic substrate S-2251 was added. Changes in absorbance at a wavelength of 405 nm per unit time were measured by a spectrophotometer (Hitachi 100-50). As controls, changes in absorbance were examined likewise with respect to a sample obtained by reacting plasmin alon and a sample obtained by reacting human $\alpha_2$-PI and plasmin without adding the monoclonal antibody. The results are shown in Table 8.

TABLE 8

| Antibody | Changes in absorbance (405 nm/min.) |
| --- | --- |
| 1D10C1 | $24.8 \times 10^{-8}$ |
| 1D10C1 F(ab')2 | $24.4 \times 10^{-3}$ |
| Plasmin alone | $24.0 \times 10^{-3}$ |
| $\alpha_2$-PI and plasmin | $8.4 \times 10^{-3}$ |

The above results show that the monoclonal antibody having F(ab')2 in accordance with this invention specifically recognizes the reactive site of human $\alpha_2$-PI, and suppresses the fibrinolysis inhibiting function of human $\alpha_2$-PI.

EXAMPLE 11

Preparation of an immuonological assay reagent containing a monoclonal antibody to $\alpha_2$-PI:

First antibody

The antibody 1D10C1 obtained in Example 3 was used after it was fixed to an insoluble carrier (microtiter plate) as shown below. This antibody can specifically recognize the reactive site of $\alpha_2$-PI at which this inhibitor inhibits the fibrinolytic activity of plasmin.

19

Second antibody

The antibody 1B10G11 obtained in Example 3 was used. This antibody specifically recognizes sites of $\alpha_2$-PI other than the reactive site. It was used after labelling it with alkali phosphatase.

The monoclonal antibody 1D10C1 in a concentration of 20 micrograms/ml was left to stand at 4° C. on a microtiter plate to fix it to the plate. A buffer (15 mM $Na_2CO_3$, 35 mM $NaHCO_3$, 3 mM $NaN_3$) containing 1% bovine serum was added and the mixture was left to stand for 4 hours. The plate was then washed five times with a washing liquor (20 mM phosphafte buffer, 0.135M NaCl, 2 mM $NaN_3$, 0.05% Tween 20) containing 1% bovine serum albumin. Then, $\alpha_2$-PI diluted to various concentrations with a diluting 20 mM phosphate buffer, 0.135M NaCl). The mixture was left to stand at room temperature for 4 hours.

Figure 2:
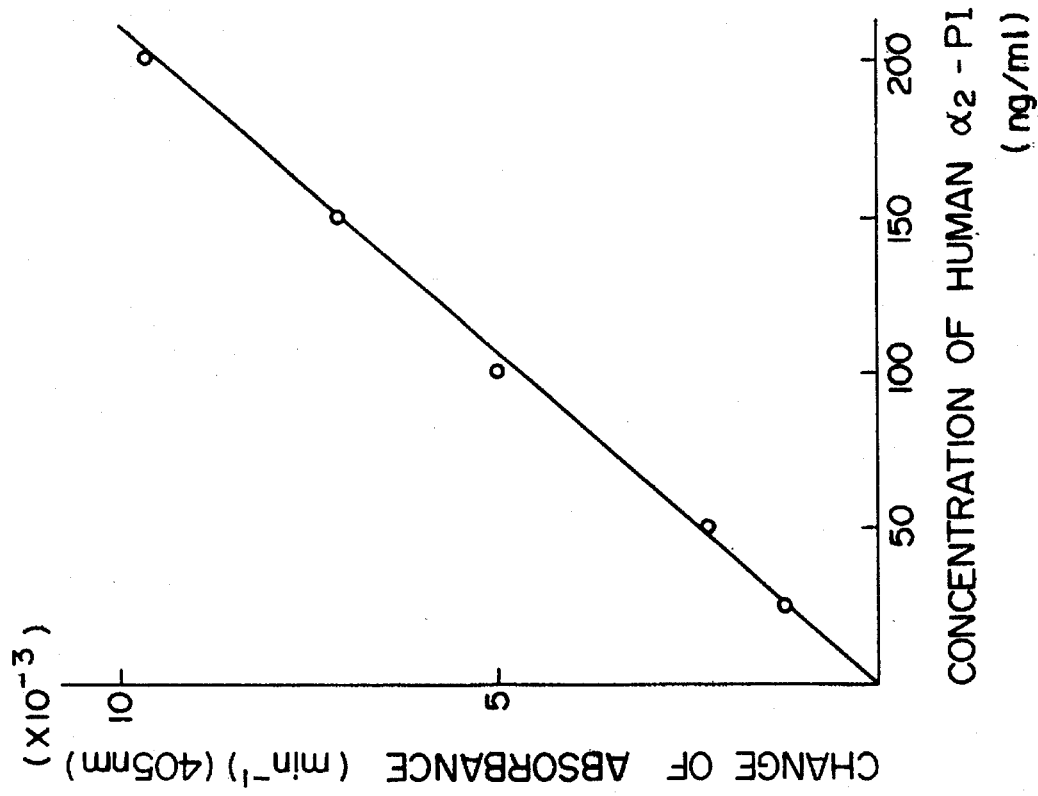
FIG. 2 is a graph showing change in absorbance based on concentration of human $\alpha_2$-PI.

The plate was then washed five times with the aforesaid washing liquor, and the alkali phosphatase-labelled monoclonal antibody, 1B10G11, which recognizes sites of $\alpha_2$-PI was added in a concentration of 329 ng/ml, followed by standing overnight at 4° C. The plate was washed with the aforesaid washing liquor, and then an alkali phosphatase substrate solution was added in a concentration of 1 mg/ml. Changes in absorbance at a wavelength of 405 nm per minute were measured. The results are shown in FIG. 2 of the accompanying drawings. It is seen from this figure that the concentration of $\alpha_2$-PI and the changes in absorbance represent a linear relation. Accordingly, by using a monoclonal antibody which specifically recognizes the reactive site of $\alpha_2$-PI as one antibody in the sandwich method, the amount of $\alpha_2$-PI can be easily measured.

EXAMPLE 12

The monoclonal antibody, 1D10C1, capable of specifically recognizing the reactive site of human $\alpha_2$-PI was used in a concentration of 20 micrograms/ml and left to stand overnight at 4° C. on a microtiter plate to fix it to the plate. A buffer (15 mM $Na_2CO_3$, 35 mM $NaHCO_3$, 3 mM $NaN_3$) containing 1% bovine serum albumin was added, and the mixture was left to stand at room temperature for 4 hours. Then, the mixture was washed five times with a washing liquor (20 mM phosphate buffer, 0.135M NaCl, 2 mM $NaN_3$, 0.05% Tween 20) containing 1% bovine serum albumin. Then, an assay sample (human plasma) diluted to various concentrations with a diluting solution (20 mM phosphate buffer, 0.135M NaCl) was added, and left to stand at room temperature for 4 hours.

Figure 3:
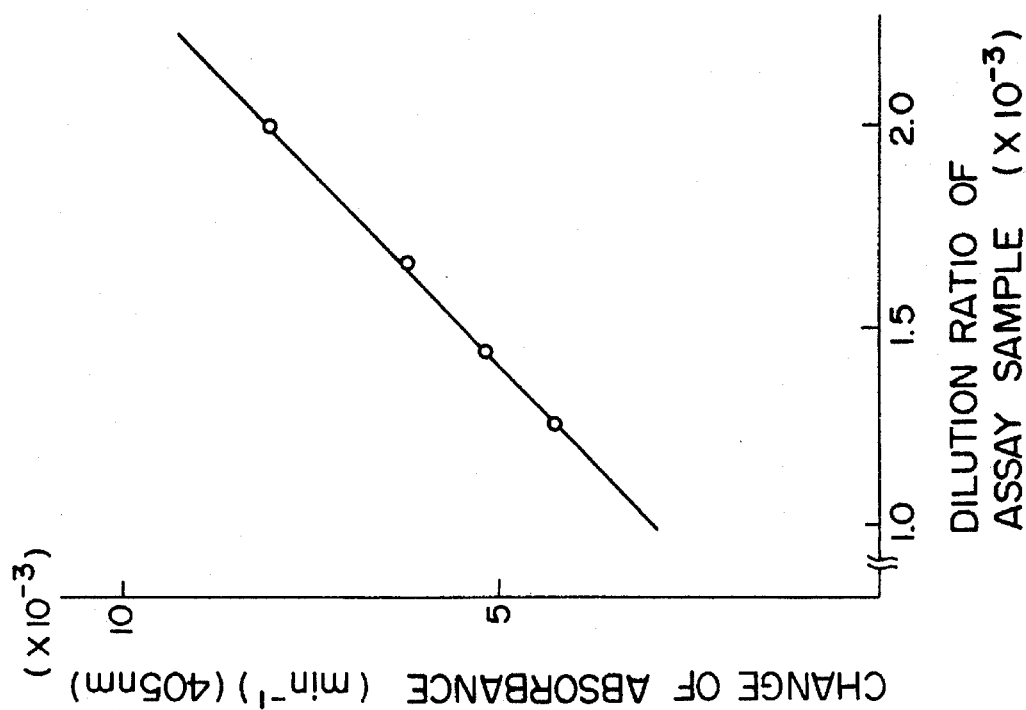
FIG. 3 is a graph showing change in absorbance based on the dilution ratio of the assay sample.

Then, the mixture was washed five times with the aforesaid washing liquor, and the alkali phosphatase-labelled monoclonal antibody, 1B10G11, which recognized sites other than the reactive site of human $\alpha_2$-PI, was added in a concentration of 329 ng/ml, and the mixture was left to stand overnight at 4° C. The mixture was washed with the aforesaid washing liquor, and an alkali phosphatase substrate solution (1 mg/ml) was added, and changes in absorbance at a wavelength of 405 nm per minute were measured by the aforesaid Elisa Analyzer. The results are plotted in FIG. 3 of the accompanying drawings. It will be understood from FIG. 3 that the ratio of dilution of the assay sample (human plasma) and the changes in absorbance represent a linear relation. Since the absorbance change value of a standard assay sample at 600-fold dilution was $6.2 \times 10^{-3}$, the concentration of human $\alpha_2$-PI in this sample was found to be 74.0 micrograms/ml (1.1 µM).

20

EXAMPLE 13

Immunological determination of $\alpha_2$-PI in human plasma in one step:

First antibody

The antibody, 1D10C1, obtained in Example 3 was used after it was fixed to an insoluble carrier (microtiter plate) in the following manner. It was a monoclonal antibody capable of specifically recognizing the reactive site of human $\alpha_2$-PI.

Second antibody

The antibody, 1B10G11, obtained in Example 3 was used after labelling it with alkali phosphatase. This antibody was a monoclonal antibody capable of specifically recognizing sites other than the reactive site of $\alpha_2$-PI.

Figure 4:
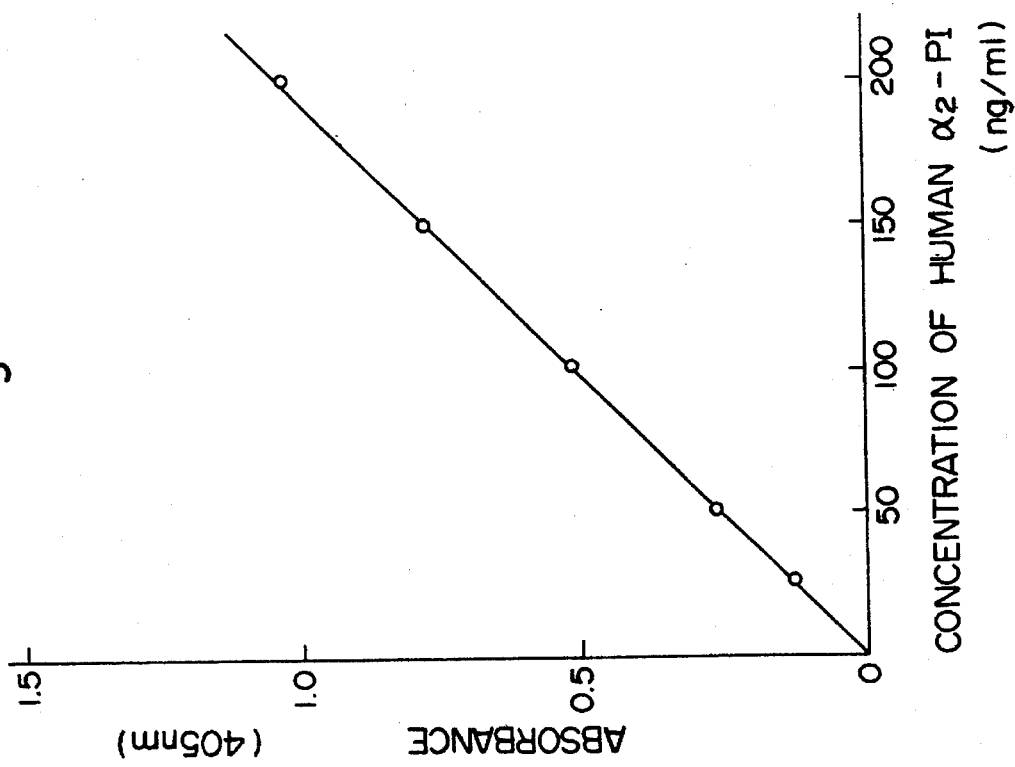
FIG. 4 is a graph showing absorbance based on concentration of human $\alpha_2$-PI.

The monoclonal antibody, 1D10C1, capable of specifically recognizing the reactive site of human $\alpha_2$-PI was used in a concentration of 20 micrograms/ml, and left to stand overnight at 4° C. on a microtiter plate to fix it to the plate. A phosphate-buffered saline containing 0.5% bovine serum albumin (to be abbreviated as 0.5% BSA-PBS) was added. The mixture was left to stand at room temperature for 2 hours, and washed three times with 0.5% BSA-PBS. A mixture composed of human plasma diluted with PBS and the alkali phosphatase-labelled monoclonal antibody, 1B10G11 in a concentration of 329 ng/ml was added, and reacted at room temperature for 2 hours. The reaction mixture was washed with 0.5% BSA-PBS, and an alkali phosphatase substrate solution was added in a concentration of 1.0 mg/ml. The mixture was reacted at room temperature for 20 minutes. Then, the absorbance of the reaction solution at a wavelength of 405 nm was measured by a microplate photometer. A calibration curve was prepared by using a standard sample of purified $\alpha_2$-PI, and from the calibration curve, the amount (micrograms/ml) of $\alpha_2$-PI in the serum sample from each of the patients was calculated. FIG. 4 shows the calibration curve, and the amounts of $\alpha_2$-PI in the plasma samples of the patients are summarized in Table 9.

The concentration of $\alpha_2$-PI and the absorbance represent a linear relationship, and by the above assay method, the amount of $\alpha_2$-PI in the plasma can be accurately determined.

TABLE 9

| Assay sample | $\alpha_2$-PI (micrograms/ml) |
| --- | --- |
| [Healthy persons] | |
| SU | 63.0 |
| KO | 57.8 |
| SZ | 66.2 |
| [Patients] | |
| FU | 32.1 |
| KI | 17.9 |
| AB | 36.8 |
| AB | 36.8 |
| KI | 25.9 |
| MI | 0.6 |
| AB | 21.9 |
| AB | 54.1 |
| HI | 58.9 |
| TA | 40.3 |
| KO | 58.3 |
| YA | 48.2 |
| KA | 98.4 |
| KI | 118.8 |
| SU | 30.8 |
| SU | 24.8 |

TABLE 9-continued

| Assay sample | $\alpha_2$-PI (micrograms/ml) |
| --- | --- |
| AK | 66.4 |
| TA | 50.0 |
| KI | 16.0 |
| AK | 58.4 |
| OI | 86.4 |
| SU | 50.4 |

EXAMPLE 14

Figure 5:
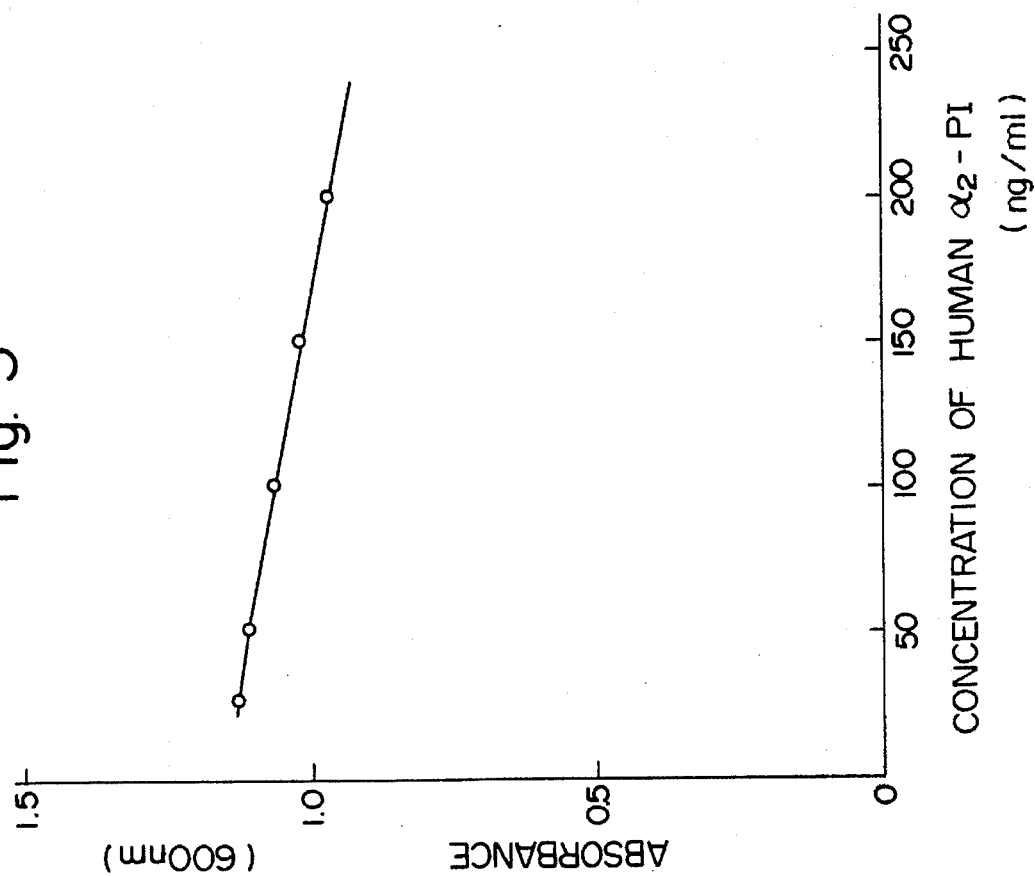
FIG. 5 is a graph showing absorbance based on concentration of human $\alpha_2$-PI

Immunological determination of the amount of $\alpha_2$-PI in human plasma by latex agglutination:

Monoclonal antibodies 1D10C1 and 1B10G11 to $\alpha_2$-PI were separately dissolved in solutions containing 0.02M glycine and 0.03M NaCl (pH 9.0) in a concentration of 50 micrograms/ml. A polystyrene latex having a particle diameter of 0.60 micrometer was suspended in each of these two antibody solutions (1.0 ml) to a concentration of 2%. The suspensions were each left to stand overnight at room temperature to adsorb the antibodies to the latices. The latices were each washed twice with a solution containing 0.02M glycine and 0.03M NaCl (pH 9.0) and then suspended in 1.0 ml of a solution containing 0.1M glycine, 0.15M NaCl, 1% BSA and 0.05% NaN$_3$ (pH 9.0). Then, 50 microliters of the latex having the monoclonal antibody 1D10C1 to $\alpha_2$-PI adsorbed thereon was mixed with 50 microliters of the latex having the monoclonal antibody 1B10G11 adsorbed thereon to form a standard sample of the latex. 100 microliters of the standard sample of the latex and an $\alpha_2$-PI standard sample in various conditions or 100 microliters of a human plasma sample diluted with a solution containing 0.1M glycine, 0.15M NaCl, 1% BSA and 0.05% NaN$_3$ (pH 9.0) were mixed, and reacted at 37° C. for 30 minutes. The reaction mixture was diluted to 125 times with a solution containing 0.1M glycine, 0.15M NaCl, 1% BSA and 0.05% NaN$_3$ (pH 9.0), and the absorbance of the diluted solution at a wavelength of 600 nm was measured. A calibration curve was prepared by using the standard $\alpha_2$-PI sample at various concenaratioins, and the amount of $\alpha_2$-PI in the human plasma sample was calculated. FIG. 5 shows the calibration curve.

Since the absorbance at 600 nm of a plasma of a healthy person diluted to 620 times was 1.068, the amount of $\alpha_2$-PI calculated by using the calibration curve was 60.8 micrograms/ml.

EXAMPLE 15

Figure 6:
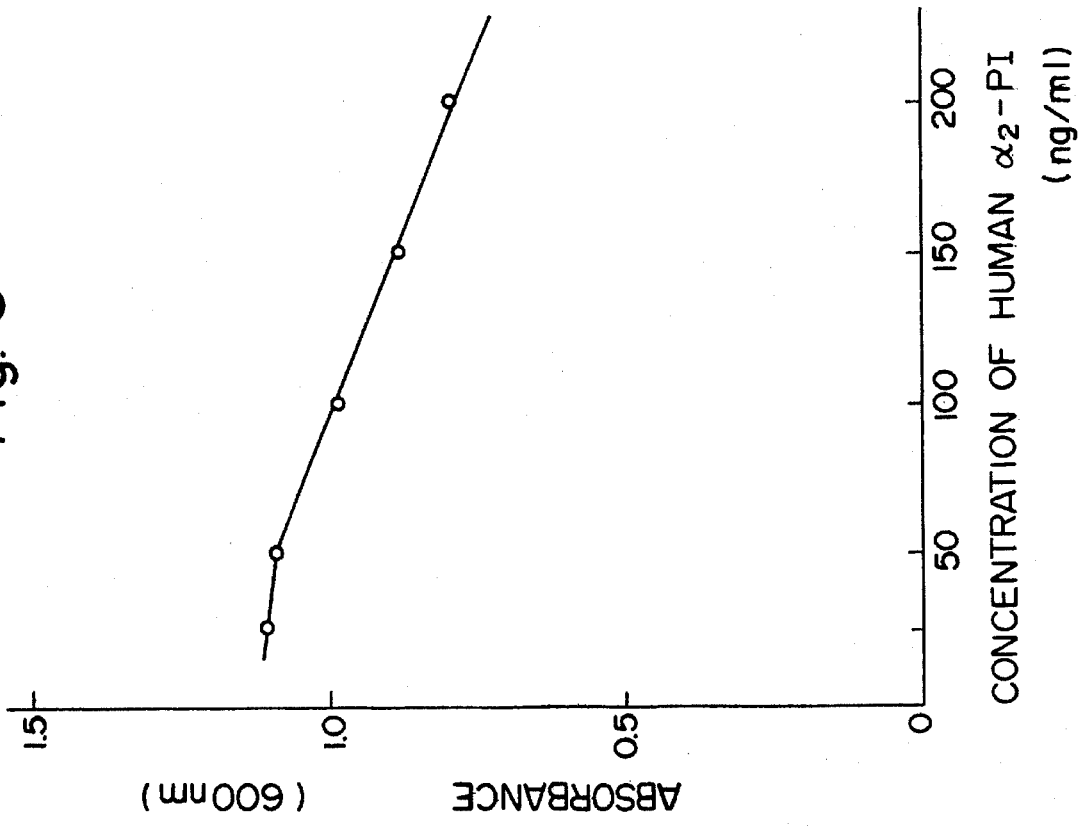
FIG. 6 is a graph showing absorbance based on concentration of human $\alpha_2$-PI.

Immunological determination of the amount of $\alpha_2$-PI of human plasma by latex agglutination:

Monoclonal antibodies, 1D10C1 and 1B10G11 to $\alpha_2$-PI were mixed so that the ratio of their concentrations became 1:1. The mixture was dissolved in a solution containing 0.02M glycine and 0.03M NaCl (pH 9.0) to prepare a solution having an antibody concentration of 50 micrograms/ml. A polystyrene latex having a diameter of 0.60 micrometer was suspended in a concentration of 2% in 1.0 ml of the antibody solution, and left to stand overnight at room temperature to adsorb the two monoclonal antibodies on the latex. The latex was washed twice with 1.0 ml of a solution containing 0.02M glycine and 0.03M NaCl (pH 9.0), and suspended in 1.0 ml of a solution containing 0.1M glycine, 0.15M NaCl, 1% BSA and 0.05% NaN$_3$ (pH 9.0). One hundred microliters of the suspension and a standard $\alpha_2$-PI sample in various concentrations or 100 microliters of a human plasma sample diluted with a solution containing 0.1M glycine, 0.15M NaCl, 1% BSA and 0.05% NaN$_3$ (pH 9.0) were mixed, and reacted at 37° C. for 30 minutes. The reaction mixture was diluted to 125 times with a solution containing 0.1M glycine, 0.15M NaCl, 1% BSA and 0.05% NaN$_3$ (pH 9.0), and the absorbance of the solution at a wavelength of 600 nm was measured. A calibration curve was prepared by using standard $\alpha_2$-PI samples in various concentrations, and the amount of $\alpha_2$-PI in the human plasma sample was calculated. FIG. 6 shows the calibration curve.

Since the absorbance of a plasma sample taken from healthy person and diluted to 620 times was 1,002, the amount of $\alpha_2$-PI calculated by using the calibration curve was 60.1 micrograms/ml.

EXAMPLE 16

Separation of $\alpha_2$-PI from human plasma:

An adsorbent (0.5 ml) having the antibody 1D10C1 obtained in Example 3 as a ligand chemically bonded thereto was packed in a column. The column was washed thoroughly with a washing liquor (50 mM buffer, pH 7.4; 0.15M NaCl), and 1.0 ml of a human plasma sample was passed through the column. The inner wall of the column was washed with 1.0 ml of the aforesaid washing liquor. The eluted fraction was designated as "pass-through fraction". The column was then washed with 2.0 ml of the same washing liquor to elute the unadsorbed substance to form a "washed fraction". The foregoing operations were all carried out at 4° C. The "pass-through fraction" and the "washed fraction" were de-salted and concentrated at 4° C.

Preparation of a calibration curve of human $\alpha_2$-PI:

The amount of $\alpha_2$-PI was measured by the method described in Example 11. Specifically, the following first and second antibodies were used.

First antibody

The antibody, 1D10C1, obtained in Example 3 was used and fixed to an insoluble carrier (microtiter plate) in the following manner. This antibody was a monoclonal antibody capable of specifically recognizing the reactive site of $\alpha_2$-PI.

Second antibody

The antibody, 1B10G11, obtained in Example 3 was used after it was labelled with alkali phosphatase. This antibody was a monoclonal antibody capable of recognizing specifically a site other than the reactive stie, of $\alpha_2$-PI.

The monoclonal antibody 1D10C1 in a concentration of 20 micrograms/ml was left to stand overnight at 4° C. on a microtiter plate and fixed to it. A buffer (15 mM Na$_2$CO$_3$, 35 mM NaHCO$_3$, 3 mM NaN$_3$) containing 1% bovine serum albumin was added and the mixture was left to stand at room temperature for 4 hours. It was then washed five times with a washing liquor (20 mM phosphate buffer, 0.135M NaCl, 2 mM NAN$_3$, 0.05% Tween 20) containing 1% bovine serum albumin, and then $\alpha_2$-PI diluted to various concentrations with a diluting solution (20 mM phosphate buffer, pH 7.4; 0.135M NaCl) was added, and the mixture was left to stand at room temperature for 4 hours.

The mixture was further washed five times with the same washing liquor as used above, and the alkali phosphatase-labelled monoclonal antibody 1B10G11 capable of recognizing a site other than the reactive site of $\alpha_2$-PI was added, and the mixture was left to stand overnight at 4° C. After washing with the same washing liquor as used above, an alkali phosphatase substrate solution was added in a concentration of 1 mg/ml. Twenty minutes later, the absorbance of the solution at a wavelength of 405 nm was measured by a microplate photometer (MTP-20 made by Corona Electrical Co., Ltd.). The results are plotted in FIG. 7. It will be seen from FIG. 7 that the concentration of $\alpha_2$-PI and the absorbance represent a linear relation. Hence, by using a monoclonal antibody capable of specifically recognizing the reactive site of $\alpha_2$-PI as one antibody in the sandwich method, the amount of $\alpha_2$-PI can be easily measured.

Figure 7:
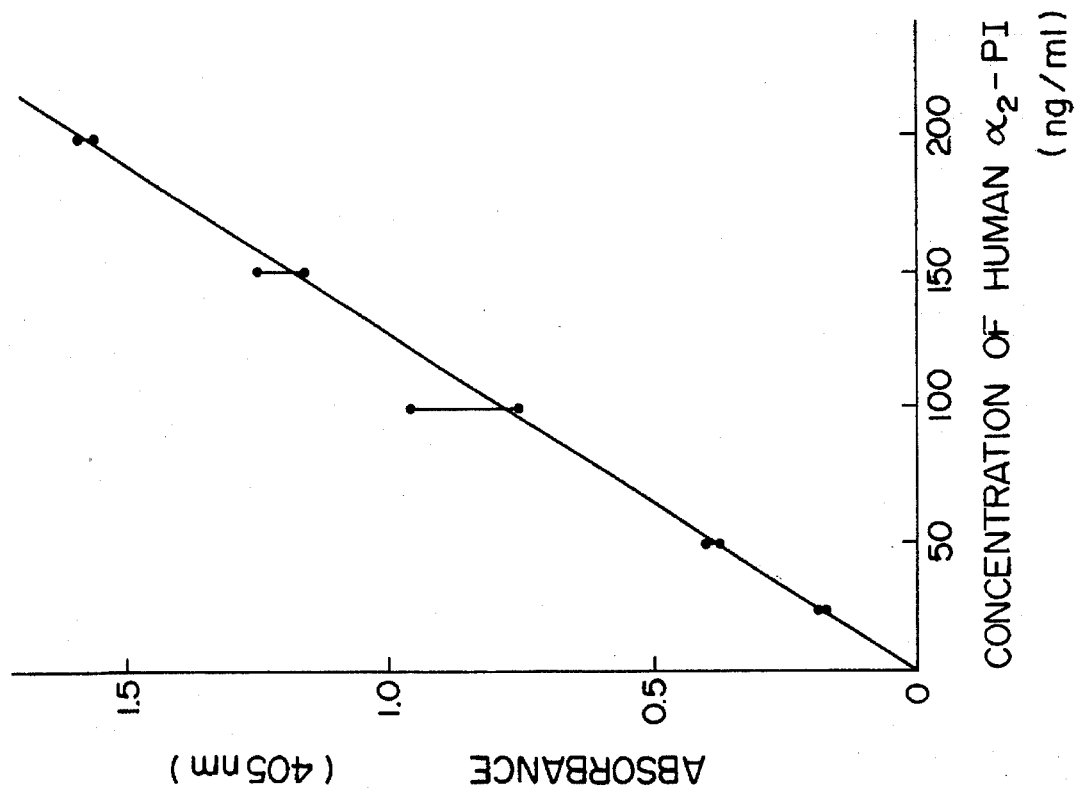
FIG. 7 is a graph showing absorbance based on concentration of human $\alpha_2$-PI.

By using FIG. 7 as a calibration curve, the amounts of $\alpha_2$-PI in the "one-pass fraction" and the "washed fraction" were measured.

Measurement of $\alpha_2$-PI in an assay sample:

The monoclonal antibody 1D10C1 capable of specifically recognizing the reactive site of human $\alpha_2$-PI was left to stand in a concentration of 20 micrograms/ml on a microtiter plate at 4° C. overnight to fix it to the plate. A buffer (15 mM $Na_2CO_3$, 35 mM $NaHCO_3$, 3 mM $NaN_3$) containing 1% bovine serum albumin was added, and the mixture was left to stand at room temperature for 4 hours. The mixture was then washed five times with a washing liquor (20 mM phosphate buffer, 0.135M NaCl, 2 mM $NaN_3$, 0.05% Tween 20) containing 1% bovine serum albumin. A sample (the "pass-through fraction", "washed fraction" and human plasma) diluted to various concentrations with a diluting solution (20 mM phosphate buffer, 0.135M NaCl) was added, and the mixture was left to stand at room temperature for 4 hours.

The mixture was washed five times with the same washing liquor as used above, and the alkali phosphatase-labelled monoclonal antibody 1B10G11 capable of recognizing a site other than the reactive site of human $\alpha_2$-PI was added. The mixture was left to stand overnight at 4° C., and washed with the same washing liquor as used above. Thereafter, an alkali phosphatase substrate solution was added in a concentration of 1 mg/ml, and 20 minutes later, the absorbance of the solution at a wavelength of 405 nm was measured by a microplate photometer (MTP-12 made by Corona Electrical Co., Ltd.).

The results are shown in Table 10. No $\alpha_2$-PI was detected from the "pass-through fraction" and the "washed fraction". It could be ascertained therefore that by adding human plasma to the adsorbent, $\alpha_2$-PI could be completely separated from human plasma.

TABLE 10

| Sample | Amount of $\alpha_2$-PI (micrograms) |
| --- | --- |
| 20 mM phosphate buffer (pH 7.4) | 0 |
| Human plasma (1.0 ml) | 59.8 |
| Pass-through fraction | 0 |
| Washed fraction | 0 |

EXAMPLE 17

Separation and elution of human $\alpha_2$-PI from human plasma using a selective adsorbent for human $\alpha_2$-PI:

An adsorbent (1.0 ml) having the monoclonal antibody 1D1DC1 to human $\alpha_2$-PI chemically combined with it was packed into a column. The column was equilibrated with a suitable buffer (0.01M sodium phosphate buffer, 0.15M NaCl, pH 7.2). Then, 2.0 ml of human plasma was passed through the column packed with the adsorbent. Fractions which were eluted without adsorption on the adsorbent were collected and used as "pass-through fraction". Then, 10 ml of the same buffer as above was passed through the column, and substances which were non-specifically adsorbed on the adsorbent were eluted and collected ("washed fraction").

Finally by using suitable eluents, human $\alpha_2$-PI bonded to the adsorbent was eluted to obtain an "eluted raction".

The following three eluents (a) to (c) were used.

(a) 50%, v/v ethylene glycol, pH 11.5

(b) 50%, v/v ethylene glycol-PBS, pH 7.4

(c) 50%, v/v ethyene glycol-PBS, 0.05% Tween 80, pH 7.4

After each elution, the column (adsorbent) was regenerated and equilibrated, and human $\alpha_2$-PI was adsorbed on the adsorbent and eluted with the next eluent. The amount of the antigen $\alpha_2$-PI in each of the "eluted fractions" obtained with the three types of eluent was determined by enzyme-linked immunosorbent assay (ELISA). The activity of $\alpha_2$-PI was determined by measuring the residual plasmin activity using a synthetic substrate S-2251 (H-D-valyl-L-leucyl-L-lysyl-p-nitroanilide dihydrochloride). The amount (micrograms) of the antigen $\alpha_2$-PI in each reaction determined by the above assay method is shown in Table 11, and the amount (micrograms) of $\alpha_2$-PI having activity determined by using the synthetic substrate is shown in Table 12.

TABLE 11

| Fraction | Eluent | | |
| --- | --- | --- | --- |
|  | (a) | (b) | (c) |
| Pass-through fraction | 0 | 0 | 0 |
| Washed fraction | 0 | 0 | 0 |
| Eluted fraction | 37.2 | 19.0 | 37.4 |

TABLE 12

| Fraction | Eluent | | |
| --- | --- | --- | --- |
|  | (a) | (b) | (c) |
| Pass-through fraction | 0 | 0 | 0 |
| Washed fraction | 0 | 0 | 0 |
| Eluted fraction | 20.1 | 15.2 | 37.2 |

The results show that the passing of the eluents (a) to (c) through the adsorbent can lead to the elution and purification of human $\alpha_2$-PI, and that particularly when (c) was used as the eluent, 37.4 micrograms which corresponded to 29.7% of $\alpha_2$-PI (126 micrograms) in 2.0 ml of the human plasma was eluted, and the amount of $\alpha_2$-PI having activity was 37.2 micrograms, indicating that the eluted $\alpha_2$-PI had an activity of about 100%.

EXAMPLE 18

Preparation of $\alpha_2$-PI in human plasma:

Human plasma (4.0 ml) was charged onto a column packed with 2.0 ml of the adsorbent described in Example 17. The column was washed in the same way as in Example 17 and eluted with the eluent (c) (50%, v/v ethylene glycol- PBS, 0.05% Tween 80, pH 7.4) to obtain an $\alpha_2$-PI fraction obtained from the human plasma. This material was concentrated and further purified by a high-performance liquid chromatographic device (HLC-803D, Toyo Soda Co., Ltd.). $\alpha_2$-PI was separated and recovered with a solvent consisting of 0.1M trifluoroacetic acid and 50% acetonitrile, and concentrated. The solvent was replaced by water, and the product was lyophilized to obtain 70.4 micrograms of a purified standard sample of $\alpha_2$-PI. SDS-polyacrylamide electrophoresis at 10% gel concentration on this standard sample led to the determination that purified $\alpha_2$-PI having a molecular weight of 67,000 could be isolated.

EXAMPLE 19

Test for dissolution of thrombus using human plasma:

Sixty microliters of a thrombin solution (200 units/ml) was added to 150 microliters of a plasma sample taken from a normal healthy human. The mixture was warmed at 37° C. for 2 minutes to coagulate the plasma to obtain a clot. Separately, 27 microliters of a solution of a monoclonal antibody to $\alpha_2$-PI (1D10C1; 3.39 mg/ml) was added to 290 microliters of a plasma sample from a normal healthy human. The mixture was warmed at 37° C. for 30 minutes. To the solution was added 100 microliters of a plasmin solution (1,000 units/ml), and simultaneously, the clot was immersed in it. The solution was then warmed at 37° C. For comparison, the above procedure was repeated using phosphate-buffered saline instead of the monoclonal antibody solution. The time periods required for dissolving the clot were compared. The use of the monoclonal antibody to $\alpha_2$-PI led to complete dissolution of the clot in about 2 hours. In the absence of the monoclonal antibody, a period of more than 10 hours was required to dissolve it.

EXAMPLE 20

Test for dissolution of thrombus by using human blood:

To 150 microliters of a blood sample taken from a normal healthy human was added 60 micrograms of a thrombin solution (200 units/ml). The mixture was warmed at 37° C. for 2 minutes to coagulate the blood and obtain a clot. Separately, 27 microliters of a solution of a monoclonal antibody to $\alpha_2$-PI (1D10C1; 3.39 mg/ml) was added, and the mixture was warmed at 37° C. for 30 minutes. To the solution was added 100 microliters of a plasmin solution (1,000 units/ml), and simultaneously, the clot was immersed in it. The solution was then warmed at 37° C. For comparison, the bove procedure was repeated using phosphate-buffered saline instead of the monoclonal antibody solution. The time periods required for dissolving the clot were compared. The use of the monoclonal antibody to $\alpha_2$-PI led to complete dissolution of the clot in about 2 hours. In the absence of the monoclonal antibody, a period of more than 10 hours was required to dissolve it.

What we claim is:

1. A monoclonal antibody specific to a human $\alpha_2$-plasmin inhibitor, said antibody having the function of specifically blocking the reactive site of the human $\alpha_2$-plasmin inhibitor, and thereby said antibody having the function of specifically blocking that site of the human $\alpha_2$-plasmin inhibitor which inhibits the fibrinolytic activity of plasmin, and of suppressing said fibrinolytic activity inhibiting function of said $\alpha_2$-plasmin inhibitor.

2. A monoclonal antibody fragment comprising at least a Fab region of a monoclonal antibody specific to a human $\alpha_2$-plasmin inhibitor, said monoclonal antibody having the function of specifically blocking the reactive site of the human $\alpha_2$-plasmin inhibitor, and thereby said monoclonal antibody having the function of specifically blocking that site of the human $\alpha_2$-plasmin inhibitor which inhibits the fibrinolytic activity of plasmin, and said fragment having the function of suppressing said fibrinolytic activity inhibiting function of the human $\alpha_2$-plasmin inhibitor.

3. A pharmaceutical composition useful for the treatment of thrombotic diseases comprising a therapeutically effective amount of the monoclonal antibody set forth in claim 1 or the monoclonal antibody fragment set forth in claim 2 and a pharmaceutically acceptable carrier therefor.

4. A hybridoma which produces the monoclonal antibody set forth in claim 1.

5. The hybridoma of claim 4 which is derived from antibody-producing cells obtained from a mammal immunized with a human $\alpha_2$-plasmin inhibitor and myeloma cells.

6. The hybridoma of claim 5 wherein the antibody-producing cells are mouse spleen cells.

* * * * *